(12) United States Patent
Suzuki et al.

(10) Patent No.: US 6,416,717 B1
(45) Date of Patent: Jul. 9, 2002

(54) EVACUATED BLOOD COLLECTION TUBE FOR RAPID BLOOD COAGULATION

(75) Inventors: Ken Suzuki, Osaka; Hironori Kondo; Manabu Iwatake, both of Yokohama, all of (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 09/384,386

(22) Filed: Aug. 27, 1999

(30) Foreign Application Priority Data

Aug. 31, 1998 (JP) .......................................... 10-245193

(51) Int. Cl.$^7$ ............................. G01N 33/49; B01L 3/14
(52) U.S. Cl. ...................... 422/102; 530/380; 530/381; 530/382; 514/2; 514/21; 435/13; 435/174; 435/177; 424/529; 424/530
(58) Field of Search ......................... 422/102; 424/529, 424/530; 435/7.5, 13, 68.1, 174, 177, 214; 514/2, 21; 530/381, 382, 383

(56) References Cited

U.S. PATENT DOCUMENTS

| | | | |
|---|---|---|---|
| 4,505,817 A | 3/1985 | Blomback et al. | 210/484 |
| 4,692,406 A | 9/1987 | Becker et al. | 435/13 |
| 5,750,657 A | * 5/1998 | Edwardson et al. | 530/382 |

FOREIGN PATENT DOCUMENTS

| | | |
|---|---|---|
| EP | 0 597 268 | 5/1994 |
| FR | 2 564 336 | 11/1985 |
| JP | 58-1460 | * 1/1983 |
| JP | 62-253036 | * 4/1987 |

OTHER PUBLICATIONS

Zucker Marcia et al., "An Evacuated Blood Collection Tube Which Facilitates High Quality Serum Preparation From Heparinized Patients For Chemistry Analysis", Jul. 17, 1994, 46th National Meeting of American Association for Clinical Chemistry, Inc XP000946583 6 1 page.

Namikata et al., "Effects of Snake Venom Batroxobin (Defibrase) On Cerebral Infarction In a Rat Model", Ome Res. Lab,. Tobishi Pharm. Co., Ltd., Tokyo, 198, Japan, vol. 20, No. 7, 1992, pp. 2393–2405, XP002045039 1 page.

English translation of Claims 1 and 2 of JP 62253036, Publication date: Nov. 4, 1987.

English translation of Claims 1 to 4 of JP 58001460, Publication date: Jan. 6, 1983.

* cited by examiner

*Primary Examiner*—David A. Reifsnyder
(74) *Attorney, Agent, or Firm*—Kubovcik & Kubovcik

(57) ABSTRACT

Providing an evacuated blood collection tube for blood collection rapidly, whereby serum of high purity can be isolated in a rapid and simple manner with no occurrence of fibrin deposition. Beads each coated with a blood coagulation-promoting enzyme comprising thrombin and batroxobin are contained in the evacuated blood collection tube. Preferably, thrombin is used in an amount of 0.1 to 3 IU and batroxobin is used in an amount of 0.25 to 2 BU, per 1 ml of collected blood.

4 Claims, No Drawings

EVACUATED BLOOD COLLECTION TUBE FOR RAPID BLOOD COAGULATION

BACKGROUND OF THE INVENTION

1. Field of the Invention

The present invention relates to an evacuated blood collection tube for rapid blood coagulation, which is suitable for isolating serum of high purity from whole blood in a rapid and simple manner.

2. Description of the Related Art

The injection of heparin as an anticoagulant agent into biological organisms has been increasing in use in recent years, according to the development and diffusion of extracorporeal blood circulation treatment such as hemodialysis. Therefore, the possibility of sampling heparinized blood by means of evacuated blood collection tubes is increased in biochemical tests for the components of blood. Generally, in the biochemical tests, serum isolated from whole blood is used as a sample. However, heparinized blood has a disadvantage such as to be scarcely coagulated.

As a method for collecting serum rapidly, there has been proposed a method for adding protamine sulfate to whole blood so as to neutralize heparin (Japanese unexamined patent publication No. 58-1460). In case of biochemical tests performed prior to hemodialysis, the blood sample contains no heparin. Therefore, the blood sample is scarcely coagulated because the protamine sulfate itself in the blood collection tube has an anti-coagulation action. For this reason, it is necessary for operators to use a blood collection tube to which protamine sulfate has not been added when the blood sample is collected prior to hemodialysis. Accordingly, the procedures have been very complex because of the selection of tubes.

Then, there has been proposed a blood collection tube which contains 10 to 200 μg of protamine sulfate and 0.1 NIH unit of thrombin as coagulation-promoting agents per 1 ml of collected blood (Japanese unexamined patent publication No. 62-253036). This blood collection tube has an advantage that blood coagulation is promoted owing to the presence of thrombin, irrespective of the presence of heparin. However, the blood collection tube is still unsatisfactory in sufficiently shortening the coagulation time because it takes about 15 minutes for blood coagulation.

SUMMARY OF THE INVENTION

The present invention has been developed to overcome the above-described disadvantages and an object of the present invention is to provide an evacuated blood collection tube for rapid blood coagulation, whereby serum of high purity can be isolated in a rapid and simple manner without fibrin deposition.

DETAILED DESCRIPTION OF THE INVENTION

As a result of assiduous studies for solving the problems in the prior art, it was found that blood samples can be coagulated rapidly by employing a blood coagulation-promoting enzyme obtained by adding a small amount of thrombin into an appropriate amount of batroxobin.

Specifically, the present invention relates to an evacuated blood collection tube for rapid blood coagulation, which contains beads, each coated with a blood coagulation-promoting enzyme comprising thrombin and batroxobin. Preferably, the amount of thrombin per 1 ml of collected blood is 0.1 to 3 IU and the amount of batroxobin per 1 ml of collected blood is 0.5 to 2 BU. Additionally, the beads are preferably made of glass or polystyrene.

DESCRIPTION OF THE PREFERRED EMBODIMENTS

The evacuated blood collection tube of the present invention contains beads, each coated with a blood coagulation-promoting enzyme comprising thrombin and batroxobin. Thrombin is relatively economical and has less influence with respect to the amount thereof on the product cost. If the amount of thrombin is too great, however, deposition of fibrin readily occurs. If no thrombin is added, alternatively, blood coagulation time is not shortened. Preferably, thrombin is added in an amount of 0.1 to 3 IU per 1 ml of collected blood. Moreover, batroxobin is so costly that the amount thereof added has a serious influence on the product cost. If the amount is too small, however, fibrin deposition readily occurs, and coagulation time is long. The amount of batroxbin can range from 0.25 to 2 BU per 1 ml of collected blood and, preferably, 0.5 to 2 BU per 1 ml of collected blood. The blood collection tube preferably contains other blood coagulation-promoting enzymes such as an appropriate amount of thromboplastin.

The beads useful in the present invention are not particularly limited as long as the beads are compatible with the blood coagulation-promoting enzyme and do not adversely affect the blood coagulation reaction or coagulation time. Glass beads and synthetic resinous beads, such as polystyrene and polypropylene, are preferably selected as the beads on which the blood coagulation-promoting enzyme is to be coated. Generally, the beads have a spherical shape. Preferably, a particle size of the beads is 0.1 to 1 mm. A specific gravity of the synthetic resinous beads is equal to or larger than the specific gravity of blood cells so that the beads can transfer to a layer of blood clot during centrifugal separation.

The present invention is now described in conjunction with the following examples.

TEST EXAMPLE 1

Glass beads coated with thrombin and batroxobin were placed in plastic containers. The amount of thrombin and batroxobin coated thereon ranged from 0 to 10 IU of thrombin and 0 to 2 BU of batroxobin, respectively, per 1 ml of collected blood. Then, the containers were sealed with a rubber stopper, to prepare a evacuated blood collection tubes for 5-ml blood collection. Next, heparin was added to blood samples collected from normal subjects, so that a final concentration of heparin became 2 IU/ml. The heparinized blood samples were taken in said evacuated blood collection tubes and the blood coagulation time was determined. The results are shown in Table 1. The blood coagulation time was defined as the time required for blood to lose fluidity when a blood collection tube was slanted.

When five minutes passed after the heparinized blood was collected in an evacuated blood collection tube, the blood was centrifuged at a rotation velocity of 3,000 rpm for 5 minutes. Then, it was observed whether fibrin was deposited in the serum layer. The results are shown in Table 2 in terms of the number of tubes out of 6 tubes in which fibrin is present in the serum. The state of fibrin deposition was observed two hours after the centrifugal separation, because the state of fibrin deposition could then be observed clearly.

From Tables 1 and 2, it is observed that the blood coagulation time can be shortened satisfactorily if the amount of batroxobin per 1 ml of collected blood is 0.5 BU or more. Further, the occurrence of the fibrin deposition can be controlled satisfactorily if the amount of thrombin is 0.1 to 3 IU.

TABLE 1

| Thrombin | Batroxobin BU | | | | |
|---|---|---|---|---|---|
| IU | 0.00 | 0.25 | 0.50 | 1.00 | 2.00 |
| 0.00 | 5 min or more | 5 min or more | 2:44 | 2:34 | 1:52 |
| 0.16 | 5 min or more | 5 min or more | 2:40 | 2:27 | 1:31 |
| 0.32 | 5 min or more | 5 min or more | 2:36 | 2:12 | 1:40 |
| 0.63 | 5 min or more | 5 min or more | 2:46 | 2:06 | 1:30 |
| 1.25 | 5 min or more | 5 min or more | 2:53 | 2:04 | 1:15 |
| 2.52 | 5 min or more | 5 min or more | 2:44 | 2:00 | 1:35 |
| 5.00 | 5 min or more | 5 min or more | 2:41 | 2:07 | 1:42 |
| 10.00 | 5 min or more | 5 min or more | 2:50 | 2:17 | 1:49 |

N = 6

TABLE 2

| Thrombin | Batroxobin BU | | | | |
|---|---|---|---|---|---|
| IU | 0.00 | 0.25 | 0.50 | 1.00 | 2.00 |
| 0.00 | 6/6 | 6/6 | 2/6 | 1/6 | 1/6 |
| 0.16 | 6/6 | 6/6 | 0/6 | 0/6 | 0/6 |
| 0.32 | 6/6 | 6/6 | 0/6 | 0/6 | 0/6 |
| 0.63 | 6/6 | 6/6 | 0/6 | 0/6 | 0/6 |
| 1.25 | 6/6 | 6/6 | 0/6 | 0/6 | 0/6 |
| 2.52 | 6/6 | 6/6 | 0/6 | 0/6 | 0/6 |
| 5.00 | 6/6 | 6/6 | 1/6 | 1/6 | 0/6 |
| 10.00 | 6/6 | 6/6 | 2/6 | 1/6 | 1/6 |

N = 6

TEST EXAMPLE 2

Blood samples collected from normal subjects were taken in the evacuated blood collection tubes the same as in Test Example 1, and the blood coagulation time was determined in the same manner as in Test Example 1. Then, the state of fibrin deposition was observed. The results are shown in Tables 3 and 4.

From Tables 3 and 4, it is observed that the blood coagulation time and the fibrin deposition can be satisfactory if the amount of batroxobin per 1 ml of collected blood is 0.25 BU or more.

TABLE 3

| Thrombin | Batroxobin BU | | | | |
|---|---|---|---|---|---|
| IU | 0.00 | 0.25 | 0.50 | 1.00 | 2.00 |
| 0.00 | 5 min or more | 3:24 | 1:38 | 1:38 | 1:32 |
| 0.16 | 5 min or more | 2:53 | 1:40 | 1:32 | 1:32 |
| 0.32 | 5 min or more | 2:35 | 1:38 | 1:20 | 1:19 |
| 0.63 | 5 min or more | 2:18 | 1:28 | 1:08 | 1:26 |
| 1.25 | 5 min or more | 2:03 | 1:26 | 1:17 | 1:17 |
| 2.52 | 5 min or more | 1:26 | 1:36 | 1:07 | 1:09 |
| 5.00 | 3:26 | 1:30 | 1:27 | 1:05 | 1:26 |
| 10.00 | 1:20 | 1:26 | 1:39 | 1:18 | 1:19 |

N = 6

TABLE 4

| Thrombin | Batroxobin BU | | | | |
|---|---|---|---|---|---|
| IU | 0.00 | 0.25 | 0.50 | 1.00 | 2.00 |
| 0.00 | 6/6 | 0/6 | 0/6 | 0/6 | 0/6 |
| 0.16 | 6/6 | 0/6 | 0/6 | 0/6 | 0/6 |
| 0.32 | 6/6 | 0/6 | 0/6 | 0/6 | 0/6 |
| 0.63 | 6/6 | 0/6 | 0/6 | 0/6 | 0/6 |
| 1.25 | 6/6 | 0/6 | 0/6 | 0/6 | 0/6 |
| 2.52 | 6/6 | 0/6 | 0/6 | 0/6 | 0/6 |
| 5.00 | 5/6 | 0/6 | 0/6 | 0/6 | 0/6 |
| 10.00 | 2/6 | 0/6 | 0/6 | 0/6 | 0/6 |

N = 6

ADVANTAGES OF THE INVENTION

As described above, it is apparent that the evacuated blood collection tube of the present invention can be used for isolating serum of high purity in a rapid and simple manner with no occurrence of fibrin deposition.

What is claimed is:

1. An evacuated blood collection tube for rapid blood coagulation, containing beads each coated with a blood coagulation-promoting enzyme comprising thrombin and batroxobin, wherein the amount of thrombin is 0.1 to 3 IU per 1 ml of collected blood and the amount of batroxobin is 0.25 to 2 BU per 1 ml of collected blood.

2. An evacuated blood collection tube according to claim 1, wherein the amount of thrombin is 0.1 to 3 IU and the amount of batroxobin is 0.5 to 2 BU per 1 ml of collected blood.

3. An evacuated blood collection tube according to claim 2, wherein each of the beads is made of glass or polystyrene.

4. An evacuated blood collection tube according to claim 1, wherein each of the beads is made of glass or polystyrene.

* * * * *